United States Patent [19]

Minaskanian

[11] Patent Number: 4,912,223
[45] Date of Patent: Mar. 27, 1990

[54] 1,4-DIHYDROPYRIDINES

[75] Inventor: Gevork Minaskanian, Irvine, Calif.

[73] Assignee: Nelson Research & Development Co., Irvine, Calif.

[21] Appl. No.: 149,541

[22] Filed: Jan. 28, 1988

[51] Int. Cl.$^4$ .......................................... C07D 491/056
[52] U.S. Cl. ..................................... 546/270; 546/15; 546/283; 546/321
[58] Field of Search ...................... 546/270, 283, 321; 514/338, 336, 356

[56] References Cited

FOREIGN PATENT DOCUMENTS 223744  5/1987  European Pat. Off. .
2577552 8/1986  France .

*Primary Examiner*—Jane T. Fan
*Attorney, Agent, or Firm*—Robert J. Baran

[57] ABSTRACT

This invention provides novel compounds represented by the general formula:

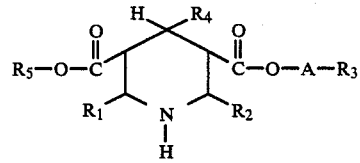

$R_1$ and $R_2$ are each independently selected from the group consisting of hydrocarbyl radicals and heteroatom-substituted hydrocarbyl radicals, wherein said heteroatoms are selected from the group consisting of nitrogen, oxygen, sulfur, phosphorus and halogen atoms; A is a straight or branched chain hydrocarbon moiety containing from 1 to 12 carbon atoms and from 0 to 2 double bonds; $R_3$ is selected from the group consisting of oxa- or dioxacycloalkanyl radicals which may be substituted with one or more hydroxy, keto, lower alkyl, phenyl or alkylenedioxy radicals; $R_4$ is an aryl or heteroaryl radical; and $R_5$ is a lower alkyl radical or A-$R_3$; and pharmaceutically-acceptable salts thereof. These compounds are useful for treating coronary insufficiency, hypertension, angina pectoris, cardiac arrythmia, heart attack, or coronary vasospasm.

6 Claims, No Drawings

1,4-DIHYDROPYRIDINES

BACKGROUND OF THE INVENTION

This invention is concerned with certain 1,4-dihydropyridines, their preparation, pharmaceutical compositions containing them and their use as therapeutic agents, particularly as anti-ischaemic and anti-hypertensive agents.

The compounds of the invention delay or prevent the cardiac contracture which is believed to be caused by an accumulation of intracellular calcium under ischaemic conditions. Calcium overload, during ischaemia, can have a number of additional adverse effects which would further compromise the ischaemic myocardium. These include less efficient use of oxygen for ATP production, activation of mitochondrial fatty acid oxidation, and possibly, promotion of cell necrosis. Thus, the compounds are useful in the treatment or prevention of cardiac conditions, such as angina pectoris, ischaemic cardiac arrythmias, heart attacks and cardiac hypertrophy. The compounds also possess vasodilator activity and are thus useful an antihypertensives and for the treatment of coronary vasospasm.

The structure and presumed mode of action of the 1,4-dihydropyridine calcium antagonists have been reviewed recently in the literature; see Meyer et al., *Annual Reports in Medicinal Chemistry*, 1983, Chapter 9 and Janis et al., *J. Med. Chem* 26, 775 (1983). One of the earliest compounds discovered, and still a standard against which new compounds are measured, is nifedipine (U.S. Pat. No. 3,485,847 to Bossert), in which the 2 and 6 positions are substituted by methyl groups, the 4 position by 2-nitrophenyl and the 3 and 5 positions by carboxylic acid methyl ester groups. Similar compounds are disclosed in U.S. Pat. Nos. 3,455,945; 3,325,505; and 3,441,468 to Loew and 3,470,297 and 3,511,837 to Bossert, which introduced variations in the 4-substituent. U.S. Pat. Nos. 3,905,970 to Bossert et al. and 3,985,758 to Marakami et al. introduced certain mono- or dialkylamino-alkylene and nitrogen-containing heterocyclic alkylene groups into one or both of the 3,5 ester groups. U.S. Pat. Nos. 4,307,103 and 4,393,070 to Sato disclose 1,4-dihydropyridines in which the 2 position is not substituted by alkyl, but instead is substituted with cyano, formyl or certain other substituents and the ester group in the 3 position may contain various substituted alkyl groups including substituted alkylaminoalkyl, heterocyclic aminoalkyl and aroylaminoalkyl, including phthalimidoethyl. U.S. Pat. No. 4,448,964 to Muto et al. discloses compounds in which the 3-position ester group contains certain substituted piperidinyl alkylene groups.

It is recognized that useful 1,4-dihydropyridines have a wide variety and specificity remains, and the effect of any particular structural modification in the properties of the compound is generally unpredictable. This is particularly true of modifications in the esters at the 3 and 5 positions, and of modifications at the 2 and 6 positions.

Moreover, there is a need for 1,4-dihydropyridines having increased solubility in water (but with no loss of activity) so that water-based pharmaceutical compositions may be prepared.

SUMMARY OF THE INVENTION

According to the invention, there are provided novel compounds of the formula:

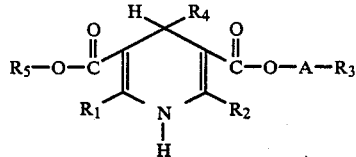

$R_1$ and $R_2$ are each independently selected from the group consisting of hydrocarbyl radicals and heteroatom-substituted hydrocarbyl radicals, wherein said heteroatoms are selected from the group consisting of nitrogen, oxygen, sulfur, phosphorus and halogen atoms;

A is a straight or branched chain hydrocarbon moiety containing from 1 to 12 carbon atoms and from 0 to 2 double bonds;

$R_3$ is selected from the group consisting of dihydroxy-, oxa- or dioxacycloalkanyl radicals which may be substituted with one or more hydroxy, keto, lower alkyl, phenyl or alkylenedioxy radicals;

$R_4$ is an aryl or heteroaryl radical; and $R_5$ is a lower alkyl radical or A-R3; and pharmaceutically-acceptable salts thereof.

Preferably, A is a radical represented by the general formula:

$$-(CH_2)_m-$$

wherein m is an integer of 1 to 12.

DETAILED DESCRIPTION OF THE INVENTION

As used herein, the term "lower" when used to modify alkyl, alkoxy, alkenyl, alkynyl, and acyl shall mean "containing not more than about 6 carbon atoms." The preferred lower alyls, alkoxys, alkenyls, alkynyls, and acyls contain not more than 4 carbon atoms.

It is particularly desirable that $R_1$ and $R_2$ be methyl. Other preferred $R_1$ and $R_2$ substituents are ethyl, n-propyl, isopropyl, n-butyl, isobutyl, t-butyl, allyl, propargyl, amino, trifluoromethyl, (lower alkyl)amino (lower alkyl), especially diethylaminoethyl and cyanomethyl.

In one preferred embodiment, $R_1$ and $R_2$ are both methyl. In another preferred embodiment, $R_1$ is methyl or ethyl and $R_2$ is not lower alkyl. In another preferred embodiment, $R_1$ is trifluoromethyl. In antoher, $R_2$ is trifluoromethyl. In yet another, both $R_1$ and $R_2$ are trifluoromethyl.

The term "5- or 6-membered saturated nitrogen-containing heterocyclic-1-yl" for $R_1$, $R_2$ and $R_3$ shall mean a heterocyclic moiety linked to the loweer alkyl group through the heterocyclic nitrogen atom, whether or not the nitrogen atom is assigned the number "1". Suitable heterocyclic moieties include pyrrolidinyl, piperazinyl, piperidinyl, 1-methyl-4-piperazinyl, morpholinyl, etc.

"Lower alylamino" for $R_1$ and $R_2$ includes methylamino, ethylamino, 1-propylamino, 2-propylamino, 1-butylamino, 2-butylamino, etc.

"Di-(lower alkyl)-amino" for $R_1$, $R_2$ and $R_3$ includes for example, dimethylamino, N-methyl-N-ethylamino, N,N-diethylamino, N,N-di-(n-propyl)amino, N-methyl-N-propylamino, etc. $R_1$, $R_2$ and $R_3$ include the named hydrocarbyl radicals wherein the hydrocarbyl radicals are substituted with hetero atoms selected from the group consisting of nitrogen, oxygen, sulfur, phosphorous and halogen atoms, particularly nitro, cyano, azido, amino trifluoromethyl, alkyl amino, dialkylamino, halo, carboxyl, carbalkoxy, alkyl, alkenyl, alkynyl, cycloalkyl, aryl, acylamino, carboxamido, sulfonamido, and $SO_m$-(lower)alkyl, wherein m is 0, 1 or 2 and a is an integer of from 0 to 3.

Examples of $R_3$ substitutents include but are not limited to methyl, ethyl, propyl, butyl, pentyl, hexyl, heptyl, octyl, nonyl, decyl, undecyl, dodecyl, 2-hydroxyethyl, 3-hydroxy-butyl, 3-hexnyl, 1,3-butadienyl, acetylenyl, allyl, ethynyl, vinyl, isopropenyl, 2-nonyl-2-butenyl, and cyanomethyl.

Preferred $R_3$ moieties are lower alkyl groups (having one to six carbon atoms), most particularly methyl, ethyl, and isopropyl, dihyroxy-, oxa- and droxacycloalkanyl radicals, which may be substituted with one or more hydroxy, keto, lower alkyl, phenyl or alkylenedroxy radicals.

A is preferably a $C_2$ to $C_6$ alkylene group, namely ethylene, propylene, butylene, pentylene, and hexylene. Preferred $R_5$ substituents are hydrogen, carboxyl, carboxamido, carb(lower) alkoxy, and lower alkyl, particularly methyl and ethyl.

$R_4$ is preferably a 3-nitrophenyl, 3-methylphenyl or a 3-trifluoromethylphenyl radical.

Said oxacycloalkanyl radical may be represented by the general formula:

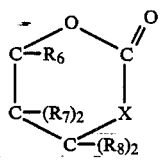

I wherein $R_6$ is selected from the group consisting of hydrogen, lower alkyl and phenyl; each $R_7$ and $R_8$ are $R_6$, or one $R_7$ and one $R_8$, together, represent a radical selected from the group consisting of alkylenedioxy or alkyl-substituted alkylenedioxy radicals and the other $R_7$ and $R_8$ are $R_6$; X represents a covalent bond or an alkenyl radical that may be substituted with one or more lower alkyl or phenyl radicals.

The dioxacycloalkanyl radical may be represented by the general formula:

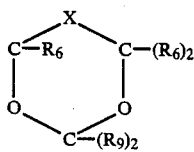

wherein X and $R_6$ are as defined above and each $R_9$ is $R_6$ or both, together, represent an alkylene radical.

Preferably, X represents a covalent bond; therefore, both the oxacycloalkanyl and the dioxacycloalkanyl radicals have a 5-membered ring or are oxacyclopentanyl or dioxacyclopentanyl radicals, respectively.

$R_6$ is preferably selected from the group consisting of hydrogen and lower alkyl radicals, i.e., alkyl radicals having from one to four carbon atoms, e.g. methyl, ethyl, isopropyl, etc. More preferably, each $R_6$ represents a hydrogen radical.

Preferably one of $R_7$ and one of $R_8$, together, represent an alkylenedioxy or an alkyl-substituted alkylene dioxy radical. More preferably $R_7$ and $R_8$, together, represent a methylene dioxy radical which may be substituted with one or more lower alkyl radicals, e.g. one or more methyl radicals.

$R_9$ preferably represents hydrogen, lower alkyl or an alkylene radical. More preferably, each $R_9$ represents a methyl radical or both, together, represent a butylene radical.

The novel compounds of formula I may be selectively hydrolyzed at the keto-substituted oxacycloalkanyl radical in the presence of a base, to yield novel hydroxycarboxylate derivatives, which have increased solubility in water as compared to the keto-substituted precursor.

The novel compounds of formula II may be selectively hydrolyzed, at the dioxacycloalkanyl radical, in the presence of an acid to yield dihydroxy derivatives i.e. 1,2 dihydroxyethyl derivatives, having increased water solubility as compared to the novel precursor compounds.

In addition, any of the above novel compounds, comprising both a keto-substituted oxacycloalkanyl radical and a dioxacycloalkanyl radical may be selectively hydrolyzed in the presence of either base or acid to convert either the keto-substituted oxacycloalkanyl radical to the hydroxycarboxylate (while leaving the dioxacycloalkanyl radical intact) or the dioxacycloalkanyl radical can be converted to a dihydroxy derivative, (while leaving the keto-substituted oxacycloalkanyl radical intact).

These compounds are useful in the treatment of coronary insufficiency, angina pectoris and hypertension.

The invention also provides pharmaceutical compositions containing the above novel compounds and a pharmaceutically acceptable carrier. Preferably these compositions are in dosage form comprising a clinically effective amount of the active compound.

The invention further provides a method of antagonizing the utilization of calcium in the body of a human being or animal and of treating the above disorders.

In another embodiment of the invention there is provided a method for preparing the novel compounds.

It will be appreciated that certain compounds of the invention are chiral due to their different ester functions. Accordingly, the invention embraces the pure enantiometers as well as mixtures thereof.

Pharmaceutically acceptable salts of the compounds of the formula are prepared in the conventional manner. Acid addition salts are derived from a therapeutically acceptable acid such as hydrochloric acid, hydrobromic acid, acetic, propionic acid and, more preferably, from a di- or poly-basic acid such as phosphoric acid, succinic acid, fumaric acid, citric acid, glutaric acid, citraconic acid, glutaconic acid, tartaric acid, maleic acid or ascorbic acid.

A preferred embodiment of this invention is a method of treatment which comprises administering a therapeutically effective amount of a compound of the above formula. In general the daily dose can be from 0.01 mg/kg to 10 mg/kg per day and preferably from 0.2 mg/kg to 4 mg/kg per day, bearing in mind, of course, that in selecting the appropriate dosage in any specific case, consideration must be given to the patient's weight, general health, metabolism, age and other factors which influence response to the drug. The parenteral dosage will be approximately an order of magnitude lower than the oral dosage. Because the activities of the compounds vary somewhat, the effective dosages will also vary.

In another embodiment of this invention there are provided pharmaceutical compositions in dosage unit form which comprise from about 1 mg to about 150 mg of a compound of the above formula, and preferably from about 5 mg to about 100 mg.

The pharmaceutical composition may be in any form suitable for oral use, such as tablets, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents elected from the group consisting of sweetening agents, flavoring agents, coloring agents, and preserving agents in order to provide a pharmaceutically elegant and palatable preparation. Tablets may contain the active ingredient in admixture with non-toxic pharmaceutically acceptable excipients which are suitable for manufacture of tablets. These excipients may be inert diluents, for example calcium carbonate, sodium carbonate, lactose, calcium phosphate; granulating and disintegrating agents, such as corn starch, gelatine or acacia; and lubricating agents, such as magnesium stearate, stearic acid or talc. The tablets may be uncoated or they may be coated by known techniques to delay disintegration and adsorption in the gastrointestinal tract and thereby provide a sustained action over a longer period.

Formulations for oral use may also be presented as hard gelatine capsules wherein the active ingredient is mixed with an inert solid diluent, for example calcium carbonate, calcium phosphate or kaoline, or as soft gelatine capsules wherein the active ingredient is mixed with an oil medium, for example, arachis oil, liquid paraffin or olive oil.

The present invention also embraces aqueous suspensions containing the active compound in admixture with suitable pharmacologically-accepted excipients. Such excipients include suspending agents, for example sodium carboxymethylcellulose, methylcellulose, hydroxypropylmethylcellulose, sodium alginate, polyvinylpyrrolidone, gum tragacanth and gum acacia; dispersing or wetting agents such as a naturally-occurring phosphatide, for example lecithin, or a condensation product of an alkylene oxide with fatty acids, for example polyoxyethylene stearate, or condensation products of ethylene oxide with long chain aliphatic alcohols, for exaple heptadecaethyleneoxycetanol, or condensation products of ethylene oxide with partial esters derived from fatty acids and hexitol, for example polyoxyethylene sorbitol monooleate, or condensation products of ethylene oxide with partial esters derived from fatty acids and hexitol anhydrides, for example polyoxyethylene sorbitan monooleate. The aqueous suspensions may also contain one or more preservatives, for example ethyl, or n-propyl-p-hydroxybenzoate, one or more coloring agents, one or more flavoring agents, and one or more sweetening agents, such as sucrose, saccharin, aspartame, mannitol, sorbitol, or sodium or calcium cyclamate.

Dispersable powders and granules suitable for preparation of an aqueous suspension by the addition of water provide the active ingredient in admixture with a dispersing or wetting agent, suspending agent, and one or more preservatives. Suitable dispersing or wetting agents and suspending agents are exemplified by those already mentioned above. Additional excipients, for example, sweetening, flavoring, and coloring agents, may also be present.

Syrups and elixirs may be formulated with sweetening agents, for example glycerol, sorbitol or sucrose. Such formulations may also contain a demulcent, a preservative, and flavoring and coloring agents.

Due to the high water solubility of many of the above novel compounds, the pharmaceutical compositions may also be in the form of a sterile injectable solution, for example, as a sterile injectable aqueous solution. These solutions may be formulated in a conventional manner without using dispersing or wetting agents. Another advantage is that the sterile injectable preparations of this invention may be prepared as a sterile, injectable parenteral solution without using diluents or solvents, such as 1,3-butanediol or propylene glycol.

The pharmaceutical compositions may be tableted or otherwise formulated so that for every 100 parts by weight of the composition there are present between 5 95 parts by weight of the active ingredient and preferably between 25 and 85 parts by weight of the active ingredient. The dosage unit form for humans will generally contain between about 1 mg and 100 mg of the active ingredient of the formula set forth above.

From the foregoing discussion of formulations it is apparent that the compositions of this invention can be administered orally or parenterally. The term parenteral as used herein includes subcutaneous injection, intravenous, intramuscular, or intrasternal injection or infusion techniques.

The compounds of the present invention may also be administered transdermally with the use of an appropriate transdermal vehicle. The preferred vehicle is 1-n-dodecylazacycloheptan-2-one, as disclosed in U.S. Pat. No. 4,405,616.

This invention also includes a method for treating coronary insufficiency (poor circulation, due to cardiac hypertrophy or to other causes), hypertension, angina pectoris, cardiac arrythmia, heart attack, or coronary vasospasm by administering an effective amount of a compound of the present invention. The invention also encompasses a method for effecting calcium channel antagonist activity in a mammal, such as a human, by administering an effective amount of a compound represented by the above formula.

The compounds represented by the formula above may be prepared by the methods used in the Examples, below:

The invention is further illustrated by the following examples, which are illustrative of various aspects of the invention, and are not intended as limiting the scope of the invention as defined by the appended claims.

EXAMPLE 1

A. Preparation of 3-Oxo-(2,2-dimethyl-1,3-dioxolan-4-yl)butanoic acid, methyl ester A mixture of 47.04 g (0.036 mol) of Solketal and 92.6 g (0.71 mol) of ethyl acetoacetate was heated in an oil bath with 50 mg of sodium metal at 145° C. for 6 hours. Ethanol was continuously removed by flowing nitrogen through the flask during the course of the reaction and the residual ethanol was removed under high vacuum. The remaining oil was distilled under high vacuum to give the product as 56.5 g (73%) of a pale yellow oil; having a b.p. of 100°–105° C./0.1 mm Hg.

B. Preparation of 2,6-Dimethyl-3-(2,2-dimethyl-1,3-dioxolan-4-carbomethoxy)-4-(3-nitrophenyl)-5-carbomethoxy-1,4 dihydropyridine A solution of 5.0 g (0.023 mol) of the product of Example 1A, 3.48 g (0.023 mol) of 3-nitrobenzaldehyde and 2.67 g (0.023 mol) of methyl-3-aminocrotonate in 100 ml of 2-propanol was refluxed under nitrogen for 15 hours. The solvent was removed in vacuo and the residue was subjected to flash chromatography (silica gel, 8:2 petroleum ether/ethyl acetate). The product was isolated as 5.0 g (49%) of a fluffy hygroscopic yellow solid: NMR: (CDCl$_3$) δ 7.5 (m, 4H), 6.2 (brs, 1H), 5.0 (s, 1H), 4.0 (m, 5H), 3.5 (s, 3H), 2.3 (5, 6H), 1.3 (s, 3H), 1.25 (s, 3H).

Anal. Calcd for $C_{22}H_{26}N_2O_8$: C, 59.11; H, 5.87, N, 6.27. Observed: C, 59.37; H, 6.00; N, 6.06.

EXAMPLE 2

A. Preparation of Ribonic acid-gamma-lactone dimethyl ketal

A solution of 215.0 g (0.17 mol) of ribonic acid-gamma-lactone in 500 ml. of acetone was stirred in an ice bath, while 10 mL of concentrated sulfuric acid was added. The reaction was stirred at ambient temperature for 5 hours.

Ammonia (gas) was bubbled through the cooled solution causing a precipitate to form. The mixture was filtered and excess acetone was removed in vacuo. The material was crystallized using chloroform/petroleum ether to give 11.6 g (43%) of product: m.p. 135–137; NMR: (CDCl$_3$) δ 4.7 (s, 2H), 4.5 (t, 1H), 3.8 (m, 2H), 2.8 (s, 1H), 1.5 (s, 3H), 1.4 (s, 3H).

B. Preparation of Ribonic acid gamma-lactone dimethyl ketal acetoacetate

A mixture of 7.6 g (0.041 mol) of the product of Example 2A and 20.35 g (0.156 mol) of ethyl acetoacetate was heated at 120° C. for 24 hours. Ethanol was removed with nitrogen flow through the flask during the course of the reaction and the residual ethanol was removed under high vacuum. Excess ethyl acetoacetate was removed by distillation and the remaining solid was subjected to flash chromatography (silica gel, 7:3 petroleum ether/ethyl acetate). The isolated product was triturated with diethyl ether, and dried under high vacuum to yield 6.75 g (60.5%) of a white powder: m.p. 66°–69° C.; NMR: (CDCl$_3$) 4.68 (m, 3H), 4.29 (m, 2H), 3.47 (s, 2H), 2.25 (s, 3H), 1.4 (d, 6H).

C. Preparation of 2,6-Dimethyl-3-(carboriboxy-gamma-lactone dimethyl ketal)-4-(3-nitrophenyl)-5-carbomethoxy-1,4-dihydropyridine

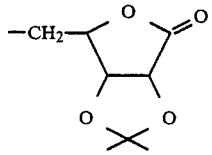

where R$_1$ is

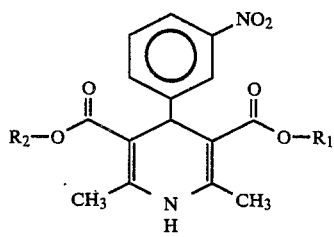

and R$_2$ is —CH$_3$.

A solution of 2.47 g (9.1 mmol) of the product of Example 2B, 1.37 g (9.1 mmol) of 3-nitrobenzaldehyde, 1.04 g (9.1 mmol) of methyl-3-aminocrotonate and 50 ml of 2-propanol was refluxed for 48 hours. The solvent was removed in vacuo and the residue was subjected to flash chromatography (silica gel, 8:2 petroleum ether/ethyl acetate). The product was obtained as 2.2 g (48%) of a yellow solid: m.p. 96°–100° C.; NMR: (CDCl$_3$) δ 7.55 (m, 4H), 4.87 (s, 1H), 4.32 (m, 5H), 3.55 (s, 3H), 2.23 (s, 6H), 1.37 (m, 6H).

Analysis calculated for $C_{24}H_{26}N_2O_{10}$: C, 57.37; H, 5.22; N, 5.58. Observed: C, 57.47; H, 5.32; N, 5.52.

EXAMPLE 3

A. Preparation of 3-Oxo-butanoic acid, (tetrahydro-5-oxo-2-furanyl) methyl ester The named product is prepared as in Example 2B except that 3-Dihydro-5-(hydroxymethyl)-2(3H) furanone is substituted for the alcohol of Example 2B.

B. Preparation of 2,6-Dimethyl-3-(tetrahydro-5-oxo-2-furanyl carbomethoxy)-4-(3-nitrophenyl)-5-carmethoxy-1,4-dihydropyridine

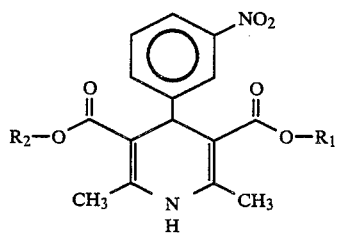

where R$_1$ is

and R$_2$ is —CH$_3$.

The named product is prepared as in Example 2C, except that the product of Example 3A is substituted for the product of Example 2B.

EXAMPLE 4

A. Preparation of 2,6-Dimethyl-5-carbomethoxy-4-(3-nitrophenyl)-3-(2,3 dihydroxycarbopropoxy)-1,4-dihydropyridine A solution of 6.5 g (0.015 mol) of the product of Example 1B, 40 mg of p-toluene sulfonic acid and 150 ml of methanol was stirred at ambient temperature for 3 days. The solvent was removed in vacuo and the resulting solid was subjected to flash chromatography (silica gel, 1:1 ethyl acetate/petroleum ether). The product was crystallized from dichloromethane/diethylether/petroleum ether to give 3.7 g (61%) of a bright yellow hygroscopic solid: m.p. 49°–53° C.; NMR: (CDCl$_3$) δ 7.5 (m, 4H), 6.3 (s, 1H), 5.0 (s, 1H), 4.0 (m, 3H), 3.4 (m, 2H), 3.5 (s, 3H), 2.3 (s, 6H).

Analysis calculated for C$_{19}$H$_{22}$N$_2$O$_8$: C, 56.15; H, 5.46; N, 6.89. Observed: C, 55.86; H, 5.60; N, 6.6.

B. Preparation of 2,6-Dimethyl-5-carbomethoxy-4-(3-nitrophenyl)-3-(1,4-dioxaspiro[4,4]non-2-yl-carbomethoxy)-1,4-dihydropyridine A solution of 2.0 g (2.5 mmol) of the product of Example 4A, 1.3 ml (15 mmol) of cyclopentanone, 40 mg of p-toluene sulfonic acid and 200 ml of toluene was refluxed for 15 hours using a Dean Stark apparatus. The solvent was removed in vacuo and the residue was subjected to flash chromatography (silica gel, 7:3 petroleum ether/ethyl acetate) to yield the product as 900 mg (40%) of a yellow hygroscopic solid: m.p. 58°–67° C.; NMR: (CDCl$_3$) δ 7.9–7.0 (m, 4H), 5.9 (s, 1H), 4.9 (s, 1H), 4.0 (m, 2H), 3.5 (s, 3H), 2.3 (s, 6H), 1.7 (brs, 8H).

Anal Calcd for C$_{24}$H$_{28}$N$_2$O$_8$: C, 61.01; H, 5.97; N, 5.93. Observed: C, 60.86; H, 6.12; N, 5.84.

EXAMPLE 5

Preparation of 2,6-Dimethyl-3,5-di-(2,2-dimethyl-1,3-dioxolan-4-carbomethoxy)-4-(3-nitrophenyl)-1,4-dihydropyridine A solution of 3.0 g (14.7 mmol) of the product of Example 1A, 1.11 g (7.34 mmol) of 3-nitrobenzaldehyde and 0.54 ml (7.94 mmol) of 17.7M ammonium hydroxide in 6 ml of absolute ethanol was refluxed under nitrogen for 6 hours. The solvent was removed in vacuo and the residue was subjected to flash chromatography (silica gel, 9:1 petroleum ether/ethyl acetate) to yield 1.36 g of a yellow solid: m.p. 44°–46° C. NMR: (CDCl$_3$) δ 7.45 (m, 4H), 6.6 (s, 1H), 5.0 (s, 1H), 3.73 (brm, 10H), 2.3 (6H, s), 1.37 (s, 12H).

Analysis calculated for C$_{27}$H$_{34}$N$_2$O$_{10}$.H$_2$O: C, 57.44; H, 6.43; N, 4.96. Observed: C, 57.58; H, 6.2; N, 4.94.

EXAMPLE 6

Preparation of 2,6-Dimethyl-3,5-di(carboriboxy-gamma-lactone dimethyl ketal)-4-(3-nitrophenyl)-1,4-dihydropyridine

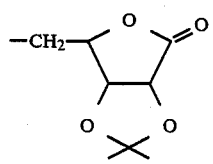

where R$_1$ is

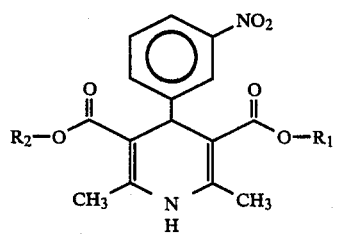

and R$_2$ is

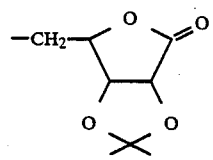

A solution of 4.94 g (18.2 mmol) of the product of Example 2B, 1.37 g (9.1 mmol) of 3-nitrobenzaldehyde and 1.48 ml (9.9 mmol) of 14.7M ammonium hydroxide in 10 ml of absolute ethanol was refluxed under nitrogen for 15 hours. The solvent was removed in vacuo and the residue was subjected to flash chromatography (silica gel, 8:2 petroleum ether/ethyl acetate). The product was obtained as 1.5 g of yellow oil: NMR: (CDCl$_3$) δ 7.4 (m, 5H), 4.45 (m, 11H), 2.35 (s, 5H), 1.35 (m, 12H).

EXAMPLE 7

Preparation of 2,6 Dimethyl-3-5-di(tetrahydro-5-oxo-2-furanylcarbomethoxy)-4-(3-nitrophenyl)-1,4-dihydropyridine

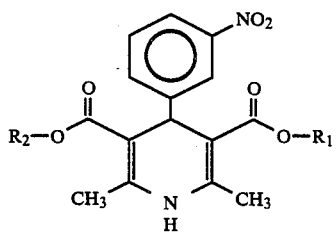

where R$_1$ is

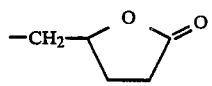

and R$_2$ is

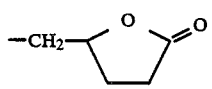

The named product is prepared as in Example 6, except that the product of Example 3A is substituted for the product of Example 2B.

EXAMPLE 8

Preparation of 2,6-Dimethyl-3-(carboriboxy-gamma-lactone)-4-(nitrophenyl)-5-carbomethoxy-1,4-dihydropyridine

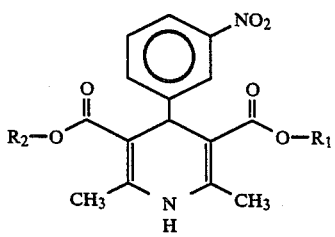

where R$_1$ is

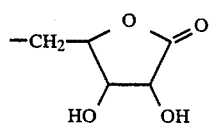

and R$_2$ is —CH$_3$.

A solution of 0.7 g (1.39 mmol) of the product of Example 2C, 10 mg of p-toluene sulfonic acid, and 25 ml of methanol was stirred at ambient temperature for 4 days. The solvent was removed in vacuo and the residue was purified by prep TLC (silica gel; 1:1 petroleum ether/ethyl acetate). The product was obtained as 20 mg of a light tan solid: NMR: (D$_2$O) δ 7.5 (m, 5H), 5.3 (s, 1H), 5.0–4.0 (m, 5H), 3.6 (s, 3H), 2.3 (m, 6H).

EXAMPLE 9

Preparation of 2,6 Dimethyl-3,5-di(2,3-dihydroxycarbopropoxy)-4-(3-nitrophenyl)-1,4-dihydropyridine A solution of 0.7 g (1.28 mmol) of the product of Example 5, 10 mg of p-toluene sulfonic acid and 50 ml of methanol was stirred under nitrogen for 1 week. The solvent was removed in vacuo and the residue was purified by prep TLC (silica gel, 95:5 ethyl acetate/methanol) to give the product as 300 mg (50%) of a yellow oil: NMR: (CDCl$_3$) δ 7.7 (m, 5H), 5.1 (s, 1H), 4.05–3.54 (brm, 10H), 2.32 (s, 6H).

EXAMPLE 10

Preparation of 2,6-Dimethyl-3,5-di(carboriboxy-gamma-lactone)-4-(3-nitrophenyl)-1,4-dihydropyridine

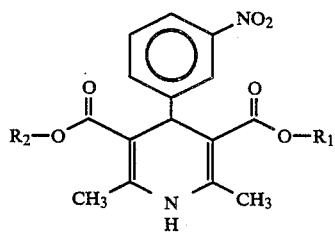

where R$_1$ is

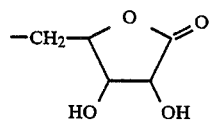

and R$_2$ is

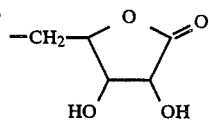

The named product is prepared as in Example 9, except that the product of Example 6 is substituted for the product of Example 5.

EXAMPLE 11

Preparation of: 2,6-Dimethyl-3-(carboribonic acid-gamma-lactone dimethylketal)(3-nitrophenyl)-5-(carbomethoxy)-1,4-dihydropyridine, sodium salt A suspension of 50 mg (0.099 mmol) of the product of Example 2C in 30 ml of water and 1.0 ml (0.099) of 0.1N NaOH was stirred at ambient temperature for 15 hours.

All material was dissolved at this time. The mixture was freeze-dried to give 50 mg (quantitative yield) of a foamy water soluble solid: m.p. 215°–220° C.

EXAMPLE 12

Preparation of 2,6-Dimethyl-3-(tetrahydro-5-oxo-2-furanylcarbomethanoicacid))-4-(3-nitrophenyl)-5-(carbo-methoxy)-1,4-dihydropyridine, sodium salt The process of Example 11 is carried out with the product of Example 3B replacing the product of Example 2C to yield the named compound.

EXAMPLE 13

Preparation of 2,6-Dimethyl-3,5-di-(carboribonic acid-gamma-lactone dimethyl ketal)-4-(3-nitrophenyl-1,4-dihydropyridine, disodium salt A suspension of 50 mg (0.076 mmol) of the product of Example 6 in 30 ml of water and 1.52 ml (0.152 mmol) of 0.1N NaOH was stirred at ambient temperature for 15 hours. The material was totally dissolved at this time. The mixture was freeze dried to give 50 mg (quantitative yield) of a foamy water-soluble solid: m.p. 225°–232° C.

EXAMPLE 14

Preparation of 2,6-Dimethyl-3,5-di(tetrahydro-5-oxo-2-furanyl carbomethanoic acid)-4-(3-nitrophenyl)-1,4-dihydropyridine, disodium salt Example 12 is repeated, substituting an equimolar amount of the product of Example 7 for the product of Example 3B to yield the named compound.

EXAMPLE 15

Preparation of 2,6-Dimethyl-3-(carboribonic acid, gamma lactone))-5-carbomethoxy-1,4 dihydropyridine, sodium salt Example 12 is repeated substituting an equimolar amount of the product of Example 8 for the product of Example 3B to yield the named compound.

EXAMPLE 16

Preparation of 2,2-Dimethyl-3,5-di(carboribonic acid, gamma lactone)-1,4 dihydropyridine, disodium salt Example 12 is repeated substituting an equimolar amount of the product of Example 10 for the product of Example 3B to yield the named compound.

EXAMPLE 17

A. The products of Examples 1A, 2B and 3A are prepared by reacting the alcohols, named in the respective examples, with a source of ketene or a diketene-acetone adduct in refluxing toluene. (See page 12, lines 7–30 of U.S. patent application Ser. No. 711,815, filed on Mar. 14, 1985, in the names of Minaskanian et al. and hereby incorporated by reference.)

B. The products of Example 17A are reacted in accordance with the process of Examples 1B, 2C and 3B, respectively, to yield the respective named compounds.

Certain of the compounds, described above, were tested for pharmacological activity in accordance with the procedures described below.

EXAMPLE 18

PHARMACOLOGY

A. Binding Assay for Drugs Acting at the DHP Site of the Calcium Channel

The assay was carried out as described by Fairhurst et al., *Life Sciences*, 32, 1331 (1983). Washed rabbit skeletal muscle membranes (fraction 2-8X) were incubated for 30 minutes at 25° C. in 2 ml final volume of medium containing 12.5 mM HEPES buffer pH 7.4 and $0.5 \times 10^{-9}$M $^3$H-nitrendipine having a specific activity of approximately 17 Ci/m mol.

Parallel experiments contained, additionally, unlabelled nifedipine at a final concentration of $10^{-6}$M, to give the non-specific binding values.

The incubation tubes were rapidly chilled in ice and the contents filtered through Whatman GF/B filters on a Millipore manifold, and the filters were placed in scintillation counting vials with 8 ml of Cytoscint cocktail, disrupted mechanically by shaking for 30 minutes and counted.

Specific binding was determined by subtracting the radioactivity in the presence of nifedipine from that in the absence of nifedipine. Drugs which interact at the DHP site will reduce this specific binding in a dose-dependent manner. The assays for the compounds of this invention were made with logarithmically spaced concentrations, the data were plotted on a probit-concentration plot, and the IC50 read off. The KI of the drug was calculated by standard techniques. The results of the assay are shown in Table I.

TABLE I

| Compound | $K_I$ (moles) |
| --- | --- |
| Example 1B | $4.5 \times 10^{-9}$ |
| Example 2C | $3.0 \times 10^{-8}$ |
| Example 4 | $1.4 \times 10^{-7}$ |
| Example 4B | $2.3 \times 10^{-9}$ |
| Example 5 | $2.9 \times 10^{-8}$ |
| Example 6 | $9.3 \times 10^{-8}$ |

TABLE I-continued

| Compound | $K_I$ (moles) |
| --- | --- |
| Nifedipine | $1.1 \times 10^{-9}$ |

EXAMPLE 19

B. Hypotensive Activity

Systolic arterial blood pressure was measured with the indirect tail cuff method in spontaneous hypertensive rates (SHR). The change in baseline pressure (170–210 mm Hg) was recorded at various time points following oral administration of 10 mmol/Kg of the test compound in polyethylene glycol. The results are given in Table II.

TABLE II

| | Hypotensive Effect (Oral Administration) Mean Change (Decrease) in Systolic Blood Pressure Minutes After Drug Administration (mm Hg) | | | | | |
| --- | --- | --- | --- | --- | --- | --- |
| No. of Animals | Compound | 12 min | 30 min | 60 min | 120 min | 240 min | 360 min |
| 2 | Example 1B | — | — | — | 36 | 34 | 19 |
| 3 | Example 5 | 17 | 19 | 13 | 17 | 19 | 19 |
| 2 | Example 4 | 13 | 16 | 18 | 12 | 6 | 4 |
| 2 | Example 2C | 40 | 37 | 31 | 29 | 22 | 20 |
| 2 | Example 4B | — | — | — | 17 | 23 | 27 |
| 2 | Nifedipine | 6 | 36 | 20 | 11 | — | — |

While particular embodiments of the invention have been described, it will be understood of course that the invention is not limited thereto since many obvious modifications can be made and it is intended to include within this convention any such modifications as will fall within the scope of the appended claims.

What is claimed is:

1. A novel compound having the structural designation 2,6-Dimethyl-3-(carboriboxy-gamma-lactone dimethyl ketal)-4-(3-nitrophenyl)-5-carbomethoxy-1,4-dihydropyridine.

2. A novel compound having the structural designation, 2,6-Dimethyl-3-(tetrahydro-5-oxo-2-furanyl carbomethoxy)-4-(3-nitrophenyl)-5-carbomethoxy-1,4-dihydropyridine.

3. A novel compound having the structural designation 2,6-Dimethyl-3,5-di(carboriboxy-gamma-lactone dimethyl ketal)-4-(3-nitrophenyl)-1,4dihydropyridine.

4. A novel compound having the structural designation 2,6-Dimethyl-3,5-di(tetrahydro-5-oxo-2-furanyl carbomethoxy)-4-(3-nitrophenyl)-1,4-dihydropyridine.

5. A novel compound having the structural designation 2,6 Dimethyl-3-(carboriboxy-gamma-lactone)-4-(nitrophenyl)-5-carbomethoxy-1,4-dihydropyridine.

6. A novel compound having the structural designation 2,6-Dimethyl-3,5-di(carboriboxy-gamma-lactone)-4-(3-nitrophenyl)-1,4-dihydropyridine.

* * * * *